(12) United States Patent
Yamanaka et al.

(10) Patent No.: US 6,211,232 B1
(45) Date of Patent: Apr. 3, 2001

(54) PROCESS FOR PRODUCING BENZAMIDOXIMES

(75) Inventors: Hiroyuki Yamanaka, Odawara; Shigeru Kojima, Minamiashigara; Isamu Kasahara, Kanagawa, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/582,744

(22) PCT Filed: Jan. 7, 1999

(86) PCT No.: PCT/JP99/00014

§ 371 Date: Jun. 29, 2000

§ 102(e) Date: Jun. 29, 2000

(87) PCT Pub. No.: WO99/35127

PCT Pub. Date: Jul. 15, 1999

(30) Foreign Application Priority Data

Jan. 8, 1998 (JP) .................................................. 10-013257

(51) Int. Cl.[7] ...................... C07C 249/04; C07C 251/48; C07C 259/10; C07C 291/06
(52) U.S. Cl. ............................................. 514/508; 564/265
(58) Field of Search ................................................ 564/265

(56) References Cited

U.S. PATENT DOCUMENTS 5,183,828 * 2/1993 van't Riet et al. .
5,621,143 4/1997 Pocius .

OTHER PUBLICATIONS

Sindelar et al., "Synthesis of (2–(PhenylThio)Phenyl)Acetamidines and Related Amidoximes as Potential Antidepressants", Collection of Czechoslovak Chemical Community, (53) 1988, p 381–387.*

Stephenson, Leslie et al., ""Reaction of some aromatic nitriles with hydroxylamine to give amides, and an alternative preparation of amidoximes" (1969)," J. Chem. Soc. C, p. 861–864, X.

* cited by examiner

Primary Examiner—Johann Richter
Assistant Examiner—Sikarl A. Witherspoon
(74) Attorney, Agent, or Firm—Louise A. Foutch; Dennis G. LaPointe; Mason & Assoc., P.A.

(57) ABSTRACT

A process for producing benzamidoximes represented by general formula (II), which are useful as intermediates of pesticides and drugs, at a stable and high yield by reacting benzonitriles represented by general formula (I) with hydroxylamine in the presence of a chelating agent wherein X represents halogeno, $C_{1-5}$alkyl, $C_{1-3}$ alkoxy, $C_{1-3}$ alkylthio, hydroxy, mercapto, amino, nitro or $C_{1-5}$haloalkyl; and n is 0 or an integer of from 1 to 5.

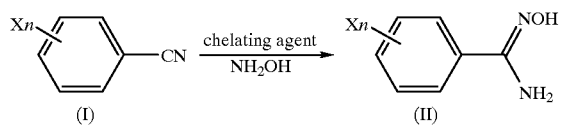

3 Claims, No Drawings

PROCESS FOR PRODUCING BENZAMIDOXIMES

FIELD OF THE INVENTION

The present invention relates to processes for the preparation of benzamidoximes useful as intermediates for agrochemicals and pharmaceuticals and represented by Formula (II)

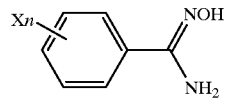

(where, X is halogen, $C_{1-5}$alkyl, $C_{1-3}$ alkoxy, $C_{1-3}$ alkylthio, hydroxyl, mercapto, amino, nitro or $C_{1-5}$ haloalkyl; and n is 0 or an integer from 1 to 5) at stable, high yields. Of the compounds produced by the processes of the present invention, 2,3-difluoro-6-trifluoromethylbenzamidoxime is particularly useful as an intermediate for agricultural and horticultural fungicides.

BACKGROUND OF THE INVENTION

It was known that amidoximes were synthesized generally by reacting nitriles and hydroxylamines (Houben-Weyl Methoden der Organischen Chemie Band VIII Sauerstoff ver Bindungen III p. 692).

It was reported that 2,3-difluoro-6-trifluoromethylbenzamidoxime, which was included in the benzamidoximes represented by Formula (II), could be produced by reacting 2,3-difluoro-6-trifluoromethylbenzonitrile with hydroxylamine hydrochloride in the presence of sodium carbonate or the like (WO 96/19442).

However, in conventional technology, if there is a very small amount of metal ions, such as iron, in a solvent or if a brown-glass or SUS vessel is used as a reaction vessel, the yield of a target amidoxime compound is strikingly reduced, and benzamides represented by Formula (III)

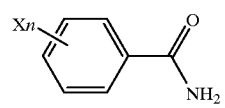

are produced in a large amount as byproducts.

DISCLOSURE OF THE INVENTION

It is an object of the present invention to produce a benzamidoxime represented by Formula (II) from a benzonitrile represented by Formula (I) and hydroxylamine at a stable, high yield.

The present invention is directed to processes for the preparation of benzamidoximes represented by Formula (II), characterized in that a benzonitrile represented by Formula (I) is reacted with hydroxylamine in the presence of a chelating agent. The reaction scheme of the present invention is shown below:

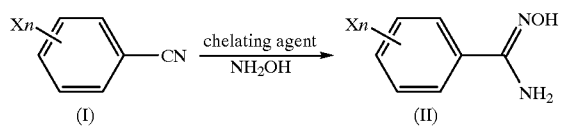

Representative examples of compounds to which the processes of the present invention are applicable are shown in Table 1.

TABLE 1

Major Representative Examples

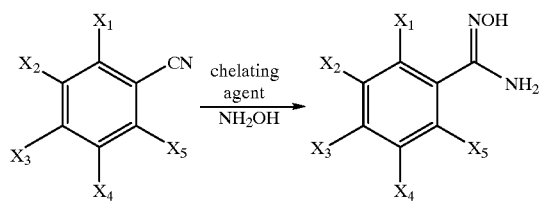

| No. | $X_1$ | $X_2$ | $X_3$ | $X_4$ | $X_5$ |
|---|---|---|---|---|---|
| 1  | F    | F   | H  | H | $CF_3$ |
| 2  | F    | H   | H  | H | $CF_3$ |
| 3  | F    | Cl  | H  | H | $CF_3$ |
| 4  | Cl   | F   | H  | H | $CF_3$ |
| 5  | Cl   | Cl  | H  | H | $CF_3$ |
| 6  | F    | F   | F  | H | $CF_3$ |
| 7  | $CF_3$ | H | H  | H | H |
| 8  | F    | H   | H  | H | H |
| 9  | F    | F   | H  | H | $CH_3$ |
| 10 | F    | F   | H  | H | $OCH_3$ |
| 11 | $CF_3$ | H | H  | F | $NH_2$ |
| 12 | $CF_3$ | H | H  | F | OH |
| 13 | Cl   | H   | H  | H | Cl |
| 14 | F    | H   | H  | H | F |
| 15 | F    | H   | H  | H | $NO_2$ |
| 16 | H    | F   | H  | H | H |
| 17 | Cl   | H   | H  | H | H |
| 18 | H    | Cl  | H  | H | H |
| 19 | H    | H   | Cl | H | H |
| 20 | H    | H   | H  | H | H |

The said reaction is carried out by reacting a benzonitrile (I) with hydroxylamine (HA) in the presence of a chelating agent. In case a reaction vessel, such as made of SUS, is used, an alkali carbonate, such as sodium hydrogencarbonate, may be present in the reaction system to protect the vessel. An amount of HA used is preferably (I):HA=1:1.5~3. HA may be used in the form of HA hydrochloride and the like in the presence of a base. It is however preferable to use free HA.

Solvents inactive to the reaction are preferably used in this invention. For example, solvents such as acetonitrile are not favorable.

Among them solvents that are highly polar and can dissolve chelating agents are preferable. For instance, a methanol-water mixed solvent is exemplified. It is more preferable to use excessive water over methanol.

Chelating agents used in the present invention are mainly those that easily form complexes with iron ions. 8-Hydroxyquinoline represented by Formula (IV) and o-phenanthroline represented by Formula (V) are preferable examples.

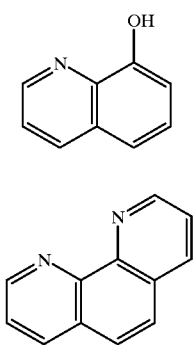

A quantitative ratio of a chelating agent may be a catalytic amount to benzonitrile (I), and more preferably 0.1 to 1 mol % to (I).

After the completion of the reaction, ordinary after-treatment gives a target compound. Particularly it is effective to extract with an acid, such as hydrochloric acid, in the said after-treatment, because of easy removal of benzamide byproducts.

BEST FORMS TO IMPLEMENT THE INVENTION

The present invention is further described in detail in reference to Examples. This invention, however, is not limited by them.

EXAMPLE 1

Reaction in a Solvent Containing an Iron Ion

In a colorless, transparent glass reaction vessel was placed a mixed solvent of 150 ml of methanol-distilled water (volume ratio 1:2) into which were dissolved beforehand 9.91 g (150 mmol) of 50% hydroxylamine aqueous solution, 99 mg (0.50 mmol) of o-phenanthroline and on purpose 86 μg (0.00068 mmol) of iron(II) chloride. Into the mixed solvent was added 10.36 g (50.0 mmol) of 2,3-difluoro-6-trifluoromethylbenzonitrile (I"). The reaction temperature stood at 60° C. for 6 hours and was returned to room temperature. When the reaction solution was analyzed with HPLC [column: Inertsil ODS—34.6 mm ø×250 mm (GL Sciences Inc.), mobile phase; $CH_3CN$—$H_2O$—10% $H_3PO_4$ 500:500:10 (v/v/v), flow rate; 1.0 ml/min, detection wavelength; 225 nm, and the same conditions for Example 2 and after], it was shown that (I") (tR 16.0 min) disappeared, 2,3-difluoro-6-trifluoromethylbenzamidoxime (II') was mainly produced (yield 76.9%, tR 3.6 min) and 2,3-difluoro6-trifluoromethylbenzamide (III') was produced as a byproduct (yield 8.4%, tR 4.8 min).

EXAMPLE 2

Reaction in an SUS Reaction Vessel

Into an SUS reaction vessel was placed a mixed solvent of 1.5 L of methanol-water (volume ratio 1:2, tap water was used as water) into which 99.09 g (1.50 mol) of 50% hydroxylamine aqueous solution and 198 mg (1.00 mmol) of o-phenanthroline were dissolved beforehand. Into the mixed solvent was added 103.56 g (500 mmol) of 2,3-difluoro-6-trifluoromethylbenzonitrile (I"). The reaction temprature stood at 60° C. for 7 hours and was returned to room temperature. In HPLC analysis of the reaction solution, it was shown that (I") disappeared, 2,3-difluoro-6-trifluoromethylbenzamidoxime (II') was mainly produced (yield 78.9%) and 2,3-difluoro6-trifluoromethylbenzamide (III') was produced as a byproduct (yield 9.0%).

COMPARATIVE EXAMPLE 1

Reaction in a Solvent Containing an Iron Ion

In a colorless, transparent glass reaction vessel was placed a mixed solvent of 150 ml of methanol-distilled water (volume ratio 1:2) into which were dissolved beforehand 9.91 g (150 mmol) of 50% hydroxylamine aqueous solution and on purpose 86 μg (0.00068 mmol) of iron(II) chloride. Into the mixed solvent was added 10.36 g (50.0 mmol) of 2,3-difluoro-6-trifluoromethylbenzonitrile (I"). The reaction temperature stood at 60° C. for 6 hours and was returned to room temperature. In HPLC analysis of the reaction solution, it was shown that (I") disappeared, 2,3-difluoro-6-trifluoromethylbenzamidoxime (II') was mainly produced (yield 62.4%) and 2,3-difluoro-6-trifluoromethylbenzamide (III') was noticeably produced as a byproduct (yield 22.8%).

COMPARATIVE EXAMPLE 2

Reaction in an SUS Reaction Vessel

Into an SUS reaction vessel was placed a mixed solvent of 1.5 L of methanol-water (volume ratio 1:2, the same tap water as that used in Example 2 was used as water) into which 99.09 g (1.50 mol) of 50% hydroxylamine aqueous solution was dissolved beforehand. Into the mixed solvent was added 103.56 g (500 mmol) of 2,3-difluoro-6-trifluoromethylbenzonitrile (I"). The reaction temperature stood at 60° C. for 7 hours and was returned to room temperature. In HPLC analysis of the reaction solution, it was shown that (I") disappeared, 2,3-difluoro-6-trifluoromethylbenzamidoxime (II') was mainly produced (yield 63.2%) and 2,3-difluoro-6-trifluoromethylbenzamide (III') was noticeably produced as a byproduct (yield 16.6%).

The effects of chelating agents depending on differences in reaction conditions, including the results of Comparative Examples, are shown in Table 2, with the reactions of 2,3-difluoro-6-trifluoromethylbenzonitrile (I") as examples.

TABLE 2

Effects of Chelating Agents

| Conditions* | Chelating agent | Product (%) (II') | (III') | Remarks |
| --- | --- | --- | --- | --- |
| Tap water used | None | 66.4 | 18.2 | |
| $FeCl_2$ added | None | 62.4 | 22.8 | Comparative Example 1 |
| SUS vessel | None | 63.2 | 16.6 | Comparative Example 2 |
| HA hydrochloride, NaOH | None | 62.1 | 27.8 | |
| Tap water used | (IV) | 79.3 | 7.7 | |
| Tap water used | (V) | 78.2 | 7.8 | |
| $FeCl_2$ added | (V) | 76.9 | 8.4 | Example 1 |
| SUS vessel | (V) | 78.9 | 9.0 | Example 2 |
| HA hydrochloride, NaOH | (V) | 75.7 | 10.6 | |

*Other conditions are the same as those of Example 1 unless otherwise noted.
(II'): 2,3-dichloro-6-trifluoromethylbenzamidoxime
(III'): 2,3-difluoro-6-trifluoromethylbenzamide
(IV): 8-hydroxyquinoline
(V): o-phenanthroline

EXAMPLE 3

Example of Isolation of 2,3-difluoro-6-trifluoromethylbenzamidoxime (II')

Into a 2 L four-neck flask were added 95.0 g (1.44 mol) of 50% hydroxylamine aqueous solution, 960 ml of pure water, 7.6 g (0.09 mol) of sodium hydrogencarbonate, 480 ml of methanol, 0.09 g of 8-hydroxyquinoline and 124.3 g (0.06 mol) of 2,3-difluoro-6- trifluoromethylbenzonitrile (I") at room temperature. After gradually raising temperature, the resulting solution was heated with stirring at 60° C. for 9 hours. It was conformed with HPLC that (I") (tR 16.0 min) disappeared, 2,3 difluoro-6-trifluoromethylbenzamidoxime (II') was mainly produced (yield 80.3%, tR 3.6 min) and 2,3-difluoro-6-trifluoromethylbenzamide (III') was produced as a byproduct (yield 4.5%, tR 4.8min). Then, at about 45° C., methanol-water (about 800 g) in the reaction solution was removed under reduced pressure. The residue was extracted with 1.2 L of methyl-t-butylether (MTBE). The organic layer was washed with 120 ml of water, and hydrochlorinated and extracted with 300 ml of 7% hydrochloric acid. Further the organic layer was twice hydrochlorinated and extracted with 150 ml of 7% hydrochloric acid. The aqueous layers from the extraction after hydrochlorination were combined, cooled down below 15° C., neutralized with 170 g of 28% sodium-hydroxide aqueous solution, and extracted again with 300 ml of MTBE. The aqueous layer was further extracted with 300 ml of MTBE. The organic layers were combined, washed with 120 ml of water, and concentrated under reduced pressure to give 114 g of target 2,3-difluoro-6-trifluoromethylbenzamidoxime (II') (m.p. 114 to 115° C., yield 78% and purity 98.7%).

APPLICABILITY IN INDUSTRIES

As described in the above, according to the processes of the present invention, benzamidoximes can be obtained at stable, high yields from benzonitriles and hydroxylamine. In other words, the addition of a chelating agent results in removing changing factors of yield decreases in this reaction, due to the mixing-in and elution of an infinitesimal amount of metal ions, such as iron. It is also effective to remove restrictions on materials of reaction vessels used for this reaction and to extend usable materials. Therefore the processes of the present invention are industrially excellent processes.

What is claimed is:

1. A process for the preparation of a benzamidoxime represented by Formula (II)

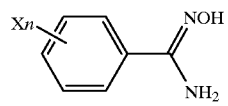

(II)

characterized in that a benzonitrile represented by Formula (I)

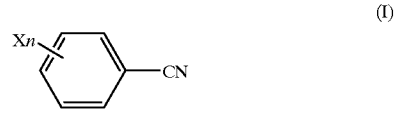

(I)

where X is halogen, $C_{1-5}$alkyl, $C_{1-3}$ alkoxy, $C_{1-3}$ alkylthio, hydroxyl, mercapto, amino, nitro or $C_{1-5}$ haloalkyl; n is 0 or an integer from 1 to 5 is reacted with hydroxylamine in the presence of a chelating agent.

2. A process according to claim 1, in which the benzonitrile represented by Formula (I)

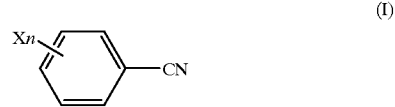

(I)

is a benzonitrile represented by Formula (I')

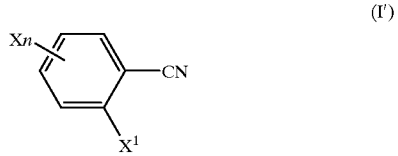

(I')

where $X^1$ is halogen or haloalkyl, n' is 0 or an integer from 1 to 4 and X is as defined above.

3. A process according to claim 1 or 2, in which the benzonitrile represented by Formula (I)

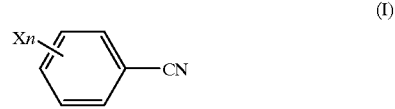

(I)

is 2,3-difluoro-6-trifluoromethylbenzonitrile.

* * * * *

UNITED STATES PATENT AND TRADEMARK OFFICE
CERTIFICATE OF CORRECTION

PATENT NO. : 6,211,232 B1
DATED : April 3, 2001
INVENTOR(S) : Hiroyuki Yamanaka et al.

It is certified that error appears in the above-identified patent and that said Letters Patent is hereby corrected as shown below:

<u>Title page,</u>
Item [75] Inventors replace "Odawara" with -- Kanagawa --.
Item [75] Inventors replace "Minamiashigari" with -- Kanagawa --.

Signed and Sealed this

Twenty-third Day of October, 2001

Attest:

NICHOLAS P. GODICI
Attesting Officer
Acting Director of the United States Patent and Trademark Office